US011723406B2

(12) United States Patent
Newton

(10) Patent No.: US 11,723,406 B2
(45) Date of Patent: Aug. 15, 2023

(54) PERSONAL VAPORIZER CARTRIDGE WITH TAMPER RESPONSIVE RESERVOIR

(71) Applicant: Kyle D. Newton, Colleyville, TX (US)

(72) Inventor: Kyle D. Newton, Colleyville, TX (US)

(*) Notice: Subject to any disclaimer, the term of this patent is extended or adjusted under 35 U.S.C. 154(b) by 333 days.

(21) Appl. No.: 16/987,037

(22) Filed: Aug. 6, 2020

(65) Prior Publication Data
US 2022/0039466 A1 Feb. 10, 2022

(51) Int. Cl.
A24F 40/40 (2020.01)
A24F 40/10 (2020.01)
A24F 40/42 (2020.01)
A61M 11/04 (2006.01)
A61M 15/06 (2006.01)

(52) U.S. Cl.
CPC ............ *A24F 40/42* (2020.01); *A24F 40/10* (2020.01); *A61M 11/041* (2013.01); *A61M 15/06* (2013.01)

(58) Field of Classification Search
CPC .......... A24F 40/10; A24F 40/40; A24F 40/42; A61M 11/041; A61M 15/0061; A61M 15/0071; A61M 15/06
See application file for complete search history.

(56) References Cited

U.S. PATENT DOCUMENTS

| | | | |
|---|---|---|---|
| 8,746,240 B2 | 6/2014 | Terry et al. | |
| 8,910,630 B2 | 12/2014 | Todd | |
| 10,099,916 B2 | 10/2018 | Murison et al. | |
| 10,136,671 B2 * | 11/2018 | Kaljura | A24D 3/17 |
| 10,737,041 B1 * | 8/2020 | Adelaar | A24F 40/65 |
| 11,045,615 B2 * | 6/2021 | Reevell | A61M 15/0036 |
| 11,324,254 B2 * | 5/2022 | Aoun | F22B 1/284 |
| 2016/0021930 A1 | 1/2016 | Minskoff et al. | |
| 2016/0150828 A1 | 6/2016 | Goldstein et al. | |
| 2016/0211693 A1 | 7/2016 | Stevens et al. | |
| 2016/0309784 A1 * | 10/2016 | Silvestrini | A24F 40/48 |
| 2018/0043114 A1 | 2/2018 | Bowen et al. | |
| 2018/0117268 A1 * | 5/2018 | Selby | A61M 15/06 |
| 2018/0168230 A1 * | 6/2018 | Reevell | A24F 40/30 |
| 2019/0166911 A1 * | 6/2019 | Xu | A24D 1/002 |
| 2020/0200381 A1 * | 6/2020 | Besso | B65D 65/40 |
| 2021/0401054 A1 * | 12/2021 | Janfada | A24F 40/10 |
| 2022/0151294 A1 * | 5/2022 | Wang | A24B 15/12 |

FOREIGN PATENT DOCUMENTS

| | | | | |
|---|---|---|---|---|
| WO | WO-2020097729 A1 * | 5/2020 | ............ | A24F 40/10 |
| WO | WO-2020128491 A1 * | 6/2020 | ............ | A24F 40/40 |

* cited by examiner

*Primary Examiner* — Abdullah A Riyami
*Assistant Examiner* — Thang H Nguyen
(74) *Attorney, Agent, or Firm* — Fish & Richardson P.C.

(57) ABSTRACT

The present disclosure describes a tamper responsive cartridge which can prevent malicious or inadvertent altering of the primary substance before it is consumed by the user, either by an intervening party, or the user itself. As described herein, an altering substance can be contained in a second reservoir, separate from the primary reservoir, and configured to make access to the primary reservoir difficult without also accessing the secondary reservoir.

18 Claims, 3 Drawing Sheets

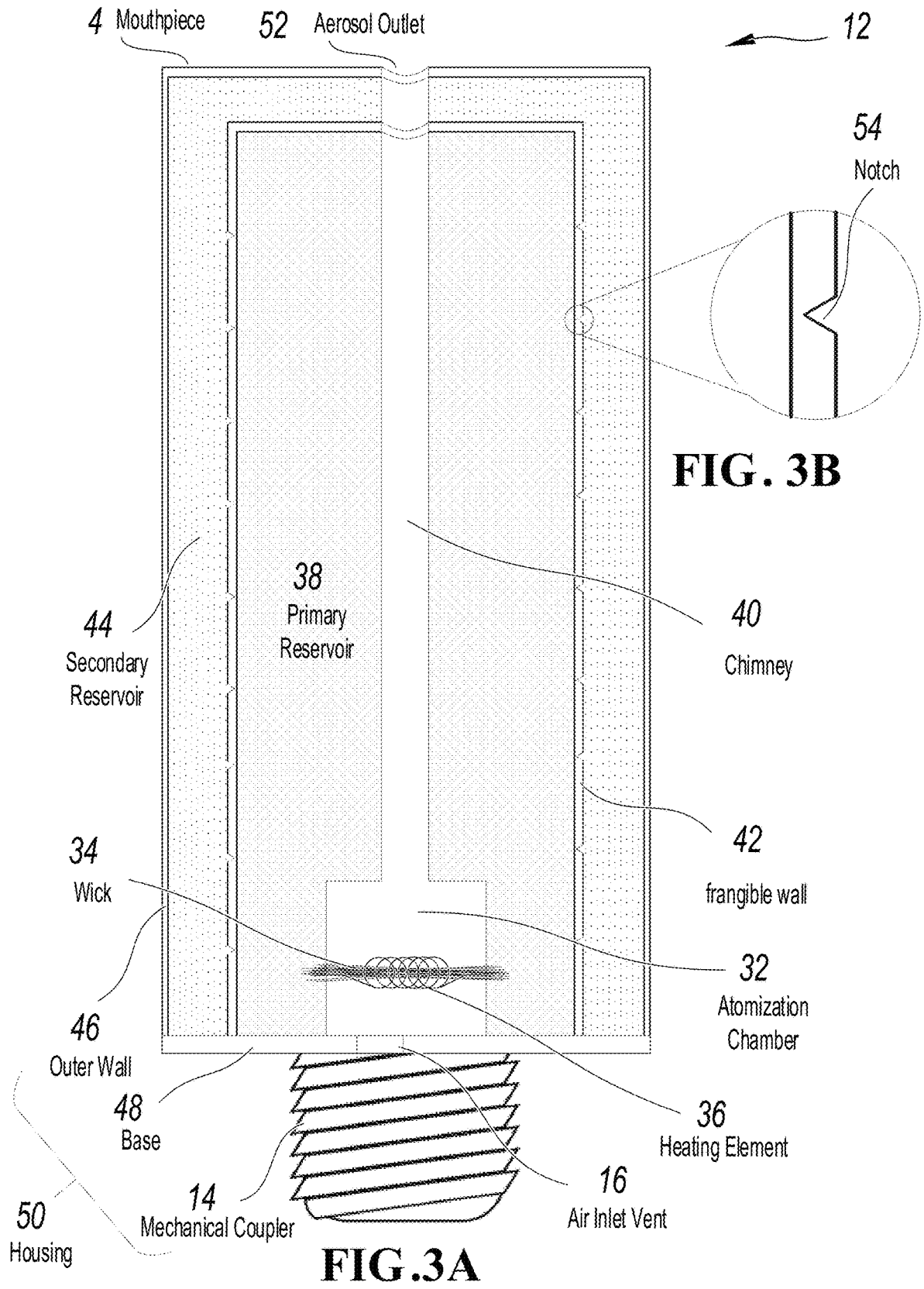

PERSONAL VAPORIZER CARTRIDGE WITH TAMPER RESPONSIVE RESERVOIR

BACKGROUND

Personal vaporizers provide an alternative to smoking techniques which involve combustion of organic matter and inhalation of the vapor. Instead vaporizers atomize a substance (e.g., a nicotine substance or cannabis substance) using a heating element to simulate the combustion found in traditional cigarettes. Personal vaporizers often use removable/replaceable cartridges containing a substance for atomization. Unauthorized or uncontrolled tampering with the cartridge or substance in the cartridge can be unsafe for the user of the personal vaporizer.

SUMMARY

The present disclosure involves systems, methods, and an apparatus for responding to tampering with the cartridge portion of a personal vaporizer. One example implementation includes a housing that has an outer wall, the housing configured to couple with a power supply portion of a personal vaporizer. The cartridge further includes a first reservoir containing a first liquid substance, the first reservoir defined by a frangible wall. A wick configured to transport the first substance from the first reservoir to an atomization chamber is further included in the cartridge. A second reservoir, containing a second substance, is defined by a space between the frangible wall and the outer wall.

Implementations can optionally include one or more of the following features.

In some instances, the atomization chamber can atomize the first substance and generate an aerosol. The atomization chamber can include a heating element and an air inlet which allows airflow through the atomization chamber into a chimney. The chimney forming a channel between the atomization chamber and an external space.

In some instances, the first reservoir and the second reservoir share a common base and removal of the common base will break the frangible wall.

In some instances, the second substance, when in contact with the first substance, chemically reduces the potency of the first substance.

In some instances, the second substance, when in contact with the first substance, forms a solid, rendering the cartridge unusable.

In some instances, the frangible wall includes one or more stress raisers. The stress raisers configured to promote breaking of the frangible wall at the stress raisers. In some implementations, the stress raisers are uniformly spaced along the frangible wall to encourage multiple breaks and even mixing of the first and second substances.

Some implementations disclosed herein include a method for responding to tampering of a cartridge of a personal vaporizer that contains a first substance to be atomized for inhalation by the vaporizer. The method includes breaking, at a frangible wall in the cartridge, in response to tampering with the cartridge, the frangible wall separating the first substance and a second substance. The method further includes releasing the second substance into the first substance, thereby altering the first substance, impairing or preventing its use.

In some instances, a differential pressure across the frangible wall induces mixing of the second substance with the first substance.

In some instances, tampering with the cartridge includes penetrating the cartridge, or removal of a base of the cartridge.

In some instances, altering the first substance includes altering at least one organoleptic property of the first substance, organoleptic properties including taste, smell, color or texture.

The details of these and other aspects and embodiments of the present disclosure are set forth in the accompanying drawings and the description below. Other features, objects, and advantages of the disclosure will be apparent from the description and drawings, and from the claims.

DESCRIPTION OF DRAWINGS

FIGS. 3A and 3B depict an example implementation of a cartridge with a tamper responsive reservoir, where FIG. 3A is a half cross-sectional view of the example cartridge and FIG. 3B is a detail view of FIG. 3A.

DETAILED DESCRIPTION

Figure 1:
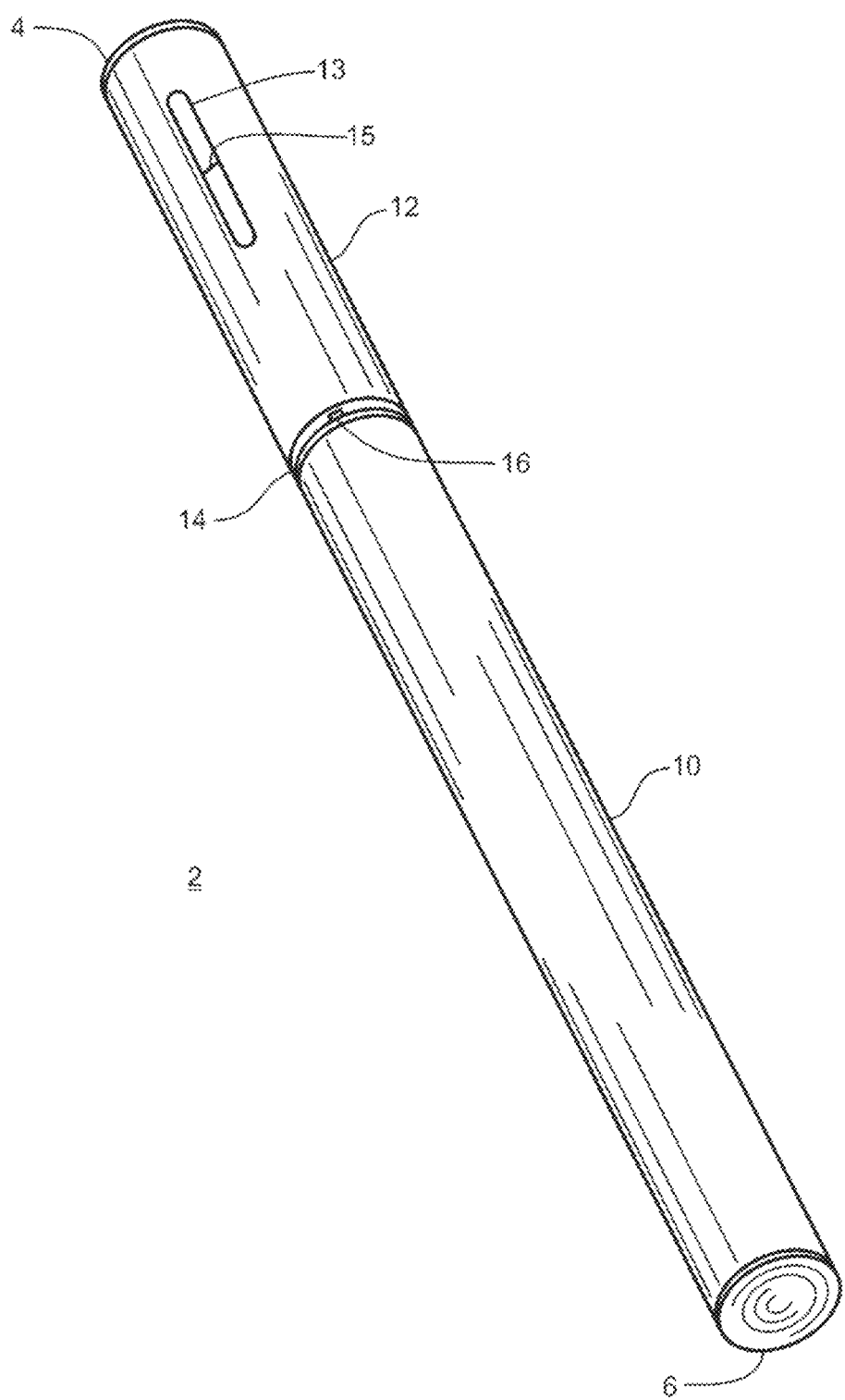
FIG. 1 depicts a perspective view of an example implementation of a personal vaporizer.

This disclosure describes a cartridge for a personal vaporizer such as an electronic cigarette, a vape pen, vape kits, e-cig, or e-hookah, electronic nicotine delivery system which is tamper responsive, the response deterring tampering with the cartridge or alteration of the substance contained within. In some implementations, personal vaporizers use removable or disposable cartridges to provide a substance to be vaporized for inhalation. Example substances can include, but are not limited to tobacco, cannabis, opium, amphetamines, or other recreational or medicinal substances. In some cases, these substances are controlled (e.g., by the manufacturer or regulated based on legal requirements) and thus it is desirable to prevent or deter tampering with the cartridge once it has been filled with the substance. A tamper responsive cartridge can prevent malicious or inadvertent altering of the primary substance before it is consumed by the user, either by an intervening party, or the user itself. As described herein, an altering substance can be contained in a second reservoir, separate from the primary reservoir, and configured to make access to the primary reservoir difficult without also accessing the secondary reservoir.

The altering substance can be one or more substances in a liquid, gas or powder form or a non-homogenous mixture thereof which can, when mixed with the primary substance, alter the primary substance and/or its performance. In certain instances, the alteration impairs or prevents the cartridge from being used in a vaporizer and/or impairs or prevents the primary substance from being used in or apart from the cartridge and vaporizer. For example, in some implementations, the alteration impairs or prevents the primary substance from being atomized by the vaporizer. Additionally or alternatively, in some implementations, the alteration can prevent removal or make removal of the primary substance from the cartridge difficult. Additionally or alternatively, in some implementations, the alteration can impair or prevent the primary substance from being ingested and/or make it unpleasant to ingest. Additionally or alternatively, the alteration can reduce or eliminate the potency of the physiological effect produced by the primary substance on a person or other animal.

In some implementations, the altering substance can include an adhesive, resin, hardening powder, and/or other solidifying material that solidifies in and around the primary substance in the cartridge. In doing so, the altering substance would impair or prevent removal of the primary substance from the cartridge by it having solidified in the cartridge and/or bonded to the walls of the cartridge. In certain instances the solidifying material can also or additionally impair or prevent the primary substance from being vaporized and/or inhaled by preventing it from flowing into the atomizing aspects of the vaporizer (e.g., the wick and heating element, discussed below) and/or rendering the primary substance non-volatile. In certain instances the solidifying material can also or additionally impair or prevent the primary substance from being ingested by rendering it difficult or impossible to be chewed and/or swallowed.

In some implementations, the altering substance can include a flavoring, irritant or other substance that adds a foul, burning or other undesirable taste or odor to the primary substance, rending it unpleasant or even painful to ingest or inhale. Some examples include, capsaicin, 1-chloroacetophenone, 2-chlorobenzylidene malononitrile, and/or other substances.

In certain implementations, where the primary substance is an opioid, the altering substance is Naloxone (e.g., Narcan®) which acts as a competitive opioid receptor antagonist, binding to opioid receptors with higher affinity than the primary substance, and preventing the body from responding to the opioids in the primary substance.

In some implementations, the altering substance can be corrosive, and its introduction into the primary reservoir can result in it coming into contact with conductive components such as electrodes or the heating element. In these implementations, the altering substance can damage or destroy the conductive components, preventing operation of the cartridge.

Turning to the illustrated example implementation, FIG. 1 is a perspective view of a personal vaporizer. While illustrated in the form factor of an electronic cigarette, the concepts herein could be applied to other types of personal vaporizers such as e-hookahs, vape kits, vape pens, etc. The example personal vaporizer 2 includes a housing having a first elongated portion 10 and a second elongated portion 12. The second elongated portion 12, also referred to as the "cartridge" in certain illustrative implementations, includes a mouthpiece end 4, which has an aerosol outlet (depicted in FIG. 3) for drawing air through the cartridge 12. The first elongated portion 10 and the second elongated portion 12 are removably joined together with a mechanical coupler 14. One or more air inlet vents 16 are provided about the coupler 14 for allowing airflow into the cartridge 12 when the user draws air through the personal vaporizer 2. The first elongated portion 10 includes a tip end 6, which in the illustrative implementation, is fabricated from a translucent material enabling the transmission of light therethrough. Within the second elongated portion 12 is disposed a liquid reservoir (not fully shown). In some implementations, the liquid reservoir includes a clear or translucent window 13 to the exterior of the housing 12 for visually determining the liquid level 15 within the liquid reservoir.

Figure 2:
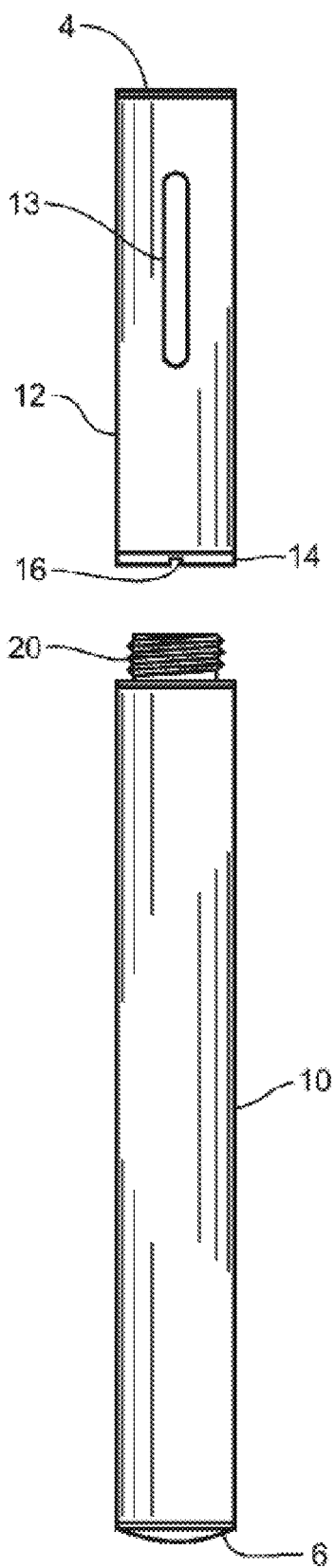
FIG. 2 depicts a side view of an example personal vaporizer with a removable cartridge removed.

FIG. 2 depicts a side view drawing, respectively, of a cartridge portion 12 and a power supply portion 10 of a personal vaporizer 2 according to an illustrative embodiment of the present invention. The mechanical coupler 14 can have two parts, one that is part of the cartridge portion 12 and one that is part of the power supply portion 10, e.g., one part being female and configured to receive the other, male, part. The mechanical coupler can be, for example, threads, a lug/channel connector, a recessed magnetic connector or other suitable means for coupling the two portions of the personal vaporizer 2. FIG. 2 shows the mechanical coupling 14 portion on the power supply portion 10 in the form of a threaded extension 20 of the housing that engages female threads of the mechanical coupler 14 portion on the cartridge portion 12. In some implementations (as shown below and discussed with reference to in FIG. 3), the cartridge 12 can include a threaded or male portion, which engages with female threads of the power supply portion 10. In addition, an electrical connection can also be facilitated in the connection between the mechanical coupler 14 parts. The power supply portion 10 can include one or more circuits for controlling operations of the cartridge portion 12. The circuits can be analog or digital and can include, for example, a microcontroller and various sensors to enable operation of the personal vaporizer 2. In this example illustration, the cartridge portion 12 can thusly be installed, uninstalled, and replaced as needed. The cartridge portion contains the liquid reservoir and the window 13 provides the visual indication as to the liquid remaining.

FIG. 3A is a half cross-sectional view of an example implementation of a tamper responsive cartridge 12. The cartridge 12 includes a housing 50 which is made up of the mechanical coupler 14 (shown with a male, threaded portion in the illustrated example), an outer wall 46, and a base 48. An atomization chamber 32 and chimney 40 are located within the housing 50, the chimney 40 extending from the atomization chamber 32 to an opening in the mouthpiece 4 of the cartridge. The atomization chamber can include a wick 34 and a heating element 36, while the chimney 40 can form the aerosol outlet 52 and provide a flow path from air inlet vent 16 through the cartridge 12. The atomization chamber 32 and chimney 40 can define an inner wall to a primary reservoir 38, which is separated from a secondary reservoir 44 by a frangible wall 42. The secondary reservoir 44 can be the space between the frangible wall 42 and the outer wall 46.

The atomization chamber 32 receives a primary substance in liquid form from the primary reservoir 38 via the wick 34. The wick 34 can be a fibrous bundle that draws liquid via capillary action from the primary reservoir 38. The wick 34 extends from the primary reservoir into the atomization chamber 32. It can be formed of a suitable heat-resistant wiking material, such as aramid, fluorocarbon, sulfide, melamine, polyimide, carbon, glass fibers, or any combination thereof. The heating element 36 can be a resistive coil that generates heat when electrical current passes through it. The heating element 36 can be supplied with electrical power from the power supply portion 10 of the personal vaporizer. The heating element 36 is located proximal to the wick 34 (in the example illustrated in FIG. 3 it is wrapped around the wick 34) heats the liquid carried from the primary reservoir 38 by the wick 34 and atomizes the primary substance which mixes with air in the atomization chamber to form an aerosol. One or more air inlet vents 16 near the bottom of the cartridge 12 allow airflow from the air inlet vent 16, through the atomization chamber 32 and out the chimney 40.

During normal operation, a user draws a suction on the cartridge via inhaling, and air enters the cartridge via the air inlet vents 16, and passes through the atomization chamber 32, where it is mixed with the primary substance which has been atomized from the wick 34 by the heating element 36 to form an aerosol. The aerosol continues up the chimney 40 and exits the cartridge 12 through the mouthpiece 4. As the primary substance on the wick 34 is depleted, more is pulled in from the primary reservoir 38 via capillary action along the wick 34.

The base 48 can support both the primary reservoir 38 and the secondary reservoir 44 and can be affixed to the frangible wall 42 in a way that is structurally stronger than the frangible wall 42. In some implementations, the frangible wall 42 can be affixed to the base 48 with an epoxy resin, or other adhesive, which ensures that any attempt at forcefully removing the base 48 will result in breaking of the frangible wall 42. Additionally or alternatively, the outer wall 46 and frangible wall 42 are affixed to the base mechanically (e.g., using a tongue and groove system and/or other mechanical connection).

The frangible wall 42 can be formed of a brittle, or readily breakable material, such as glass, ceramic, brittle plastic or other material, which is strong enough to maintain its integrity sealing the two reservoirs from one another during normal use or pressure changes, yet will readily break in response to an attempt to puncture the frangible wall 42 (e.g., with a syringe, drill, saw or otherwise), crush all or a portion of the housing 50, disconnect the frangible wall 42 or other part of the housing 50 from the base 48, or other attempts at tampering. In some implementations, the frangible wall 42 can be shaped to define stress raisers 54, such as notches (FIG. 3B) or other stress raisers, to encourage even breaking and uniform mixture of the primary substance and the altering substance when broken. In FIG. 3B, the stress raisers 54 are shown equally spaced apart along the extent of the frangible wall 42, intermediate the ends, and extend around the entire perimeter of the wall. However, in other instances, the stress raisers 54 could be arranged differently, not equally spaced, concentrated in one or more certain locations, or otherwise arranged. While illustrated at the bottom of the cartridge 12, in some implementations, the base 48 can alternately be provided as a cap located at the top of the cartridge. In some implementations the cartridge has both a cap (not shown) and a base 48. Also, the outer wall 46 and frangible wall 42 are illustrated as concentric and generally cylindrical, but they could be differently arranged, not concentric and/or configured in other shapes (e.g., rectangles, pentagons, etc.).

The secondary reservoir 44 can contain the altering substance. In FIG. 3A, the secondary reservoir 44 entirely surrounds the primary reservoir 38, except at the base 48, but in other implementations, the secondary reservoir 44 can surround more or less, or all of the primary reservoir 38. In this manner, any attempt to puncture the cartridge or otherwise access the primary reservoir 38, will result in breaking the frangible wall 42 and mixing the altering substance with the primary substance. In some implementations the secondary reservoir 44 can be hermetically sealed, preventing any particulate or fluid ingress or egress. In some implementations, one of the primary reservoir 38 or secondary reservoir 44 can be a higher pressure, in order to encourage prompt mixing of the altering substance and the primary substance if the frangible wall 42 is broken.

Although this disclosure has been described in terms of certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure.

The invention claimed is:

1. A tamper responsive cartridge for use with a power supply portion of a personal vaporizer, comprising:
   a housing comprising an outer wall, and wherein the housing is configured to couple with the power supply portion of the personal vaporizer;
   a first reservoir containing a first liquid substance, the first reservoir defined by a frangible wall, the frangible wall comprising a stress raiser intermediate its ends and configured to promote breaking at the stress raiser;
   a wick configured to transport the first substance from the first reservoir to an atomization chamber; and
   a second reservoir containing a second substance, the second reservoir defined by a space between the frangible wall and the outer wall.

2. The cartridge of claim 1, wherein the atomization chamber is configured to atomize the first substance and generate an aerosol, the atomization chamber comprising:
   a heating element; and
   an air inlet to allow airflow through the atomization chamber into a chimney, wherein the chimney forms a channel between the atomization chamber and an external space.

3. The cartridge of claim 1, wherein the first reservoir and the second reservoir share a common base, and wherein removal of the common base will break the frangible wall.

4. The cartridge of claim 1, wherein the second substance, when in contact with the first substance, forms a solid, rendering the cartridge unusable.

5. The cartridge of claim 1, wherein the second substance, when in contact with the first substance, chemically reduces the potency of the first substance.

6. The cartridge of claim 1, wherein a plurality of stress raisers are uniformly spaced to encourage multiple breaks and even mixing of the first and second substances.

7. A method for responding to tampering of a cartridge of a personal vaporizer, the cartridge containing a first substance to be atomized for inhalation by the vaporizer, the method comprising:
   fracturing, at a frangible wall in the cartridge, in response to tampering with the cartridge, the frangible wall separating the first substance and a second substance; and
   releasing the second substance into the first substance and altering the first substance, impairing or preventing its use.

8. The method of claim 7, wherein a differential pressure across the frangible wall induces mixing of the second substance with the first substance.

9. The method of claim 7, wherein tampering with the cartridge comprises penetrating the cartridge, or removal of a base of the cartridge.

10. The method of claim 7, wherein altering the first substance includes chemically reducing a potency of the first substance.

11. The method of claim 7, wherein altering the first substance comprises turning the first substance to a solid.

12. The method of claim 7, wherein altering the first substance comprises altering at least one organoleptic property of the first substance, wherein the organoleptic properties altered include at least one of taste, smell, color, or texture.

13. A system for responding to tampering of a cartridge of a personal vaporizer the system comprising:
   a housing comprising an outer wall, and wherein the housing is configured to couple with a power supply portion of the personal vaporizer;

a first reservoir containing a first liquid substance, the first reservoir defined by a frangible wall, the frangible wall comprising a stress raiser intermediate its ends and configured to promote breaking at the stress raiser;

a wick configured to transport the first substance from the first reservoir to an atomization chamber; and a second reservoir containing a second substance, the second reservoir defined by a space between the frangible wall and the outer wall, wherein the second substance, when mixed with the first substance, alters the first substance.

14. The system of claim 13, wherein the atomization chamber is configured to atomize the first substance and generate an aerosol, the atomization chamber comprising:

a heating element; and an air inlet to allow airflow through the atomization chamber into a chimney, wherein the chimney forms a channel between the atomization chamber and an external space.

15. The system of claim 13, wherein the first reservoir and the second reservoir share a common base, and wherein removal of the common base will break the frangible wall.

16. The system of claim 13, wherein the second substance, when in contact with the first substance, forms a solid, rendering the cartridge unusable.

17. The system of claim 13, wherein the second substance, when in contact with the first substance, chemically reduces the potency of the first substance.

18. The system of claim 13, wherein the stress raisers are uniformly spaced to encourage multiple breaks and even mixing of the first and second substances.

* * * * *